United States Patent
Bulan et al.

(10) Patent No.: US 6,395,165 B2
(45) Date of Patent: May 28, 2002

(54) PROCESS FOR PREPARING PERFLUORINATED ORGANIC COMPOUNDS BY ELECTROCHEMICAL FLUORINATION

(75) Inventors: Andreas Bulan, Langenfeld; Joachim Herzig, Leichlingen; Günter Lailach, Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/887,610

(22) Filed: Jun. 22, 2001

(30) Foreign Application Priority Data

Jun. 28, 2000 (DE) .......................... 100 31 565

(51) Int. Cl.[7] .............. C25B 3/08; C25B 3/00
(52) U.S. Cl. .............. 205/460; 205/430; 205/431; 205/455
(58) Field of Search ............ 205/413, 422, 205/430, 431, 436, 460, 455

(56) References Cited

U.S. PATENT DOCUMENTS

| | | | |
|---|---|---|---|
| 2,519,983 A | 8/1950 | Simons | 204/62 |
| 4,668,497 A | 5/1987 | Miki | 423/484 |
| 4,756,899 A | 7/1988 | Jenczewski et al. | 423/483 |
| 4,929,435 A | 5/1990 | Boghean et al. | 423/484 |
| 5,326,437 A | 7/1994 | Bulan et al. | 204/59 F |
| 5,616,794 A * | 4/1997 | Behr et al. | 562/851 |

OTHER PUBLICATIONS

Olah et al., "Electrophilic Fluorination of Methane with "F+" Equivalent N2F+ and NF4+ Salts", J. Am. Chem. Soc. (month unavailable, 1994), pp. 5671–5673.*

Chem–Ing–Tech. 58 (month unavailable) 1986, Nr. 1 pages 31–38, Enno Hollitzer und Peter Sartori, Die electrochemische Fluorierung–ein Überblick.

Houben Weyl, vol. 10a, Organo Fluorine Compounds, (month unavailable) 1999, Chapter 7, pp. 305–320, Electrochemical Introduction of Fluorine, K. Pohmer and A. Bulan.

* cited by examiner

Primary Examiner—Edna Wong
(74) Attorney, Agent, or Firm—Joseph C. Gil; Diderico van Eyl

(57) ABSTRACT

A novel process for the continuous preparation of perfluorinated organic compounds by electrochemical fluorination of the parent non-fluorinated or partially fluorinated organic compounds using hydrogen fluoride having an arsenic content of less than about 10 ppm can be operated over a prolonged period of time without the electrode area-time yield decreasing over time.

8 Claims, No Drawings

PROCESS FOR PREPARING PERFLUORINATED ORGANIC COMPOUNDS BY ELECTROCHEMICAL FLUORINATION

BACKGROUND

The invention relates to a process for preparing perfluorinated organic compounds by electrochemical fluorination using hydrogen fluoride having a low arsenic content.

Electrochemical fluorination is a known electrochemical process for introducing fluorine into organic compounds by reaction of the organic compounds with hydrogen fluoride. In principle, all hydrogen atoms of the organic compounds can be replaced by fluorine atoms during the course of the reaction, giving perfluorinated compounds. Partially fluorinated compounds or their downstream products and also short-chain cracking products and polymeric compounds can be formed as by-products. Compared with fluorination using elemental fluorine, electrochemical fluorination offers the advantage that functional groups of the starting compounds are retained unchanged. Depending on the length of the carbon chain of the starting materials, the yields of perfluorinated product are from 5 to 90% by weight, with the yields decreasing with longer carbon chains.

A review of electrochemical fluorination is given in E. Hollitzer P. Sartori, Chem.-Ing.-Tech. 58 (1986), No. 1, pp. 31–38 and Houben Weyl, Vol. 10a, Organo Fluorine Compounds (1999), Chapter 7. Electrochemical Introduction of Fluorine, pp. 305–318.

Since the space-time yields in electrochemical fluorination are low, it is known from the prior art that it can be advantageous to carry out electrochemical fluorination continuously.

When this process is carried out according to the above-mentioned prior art, the following disadvantages are noticeable:

On prolonged operation of an electrolysis cell, i.e. longer than three months, it is found that the electrode area-time yield of the cell at constant electrode voltage drops steadily. Here, the "electrode area-time yield" is the amount of perfluorinated target product produced per unit electrode area and per unit time. However, increasing the electrode voltage to compensate for the decreasing electrode area-time yield leads to increased electrode corrosion.

It is therefore an object of the invention to provide a process for preparing perfluorinated organic compounds which can be operated continuously over a prolonged period of time and in which the electrode area-time yield does not decrease with time.

It has now surprisingly been found that electrochemical fluorination can be carried out with a high electrode area-time yield and very low electrode corrosion if a hydrogen fluoride having a low arsenic content is used instead of commercial hydrogen fluoride, which normally contains from 15 to 500 ppm of arsenic, as raw material for the electrochemical fluorination.

SUMMARY

The invention relates to a process for continuously preparing perfluorinated organic compounds comprising electrochemical fluorinating of a parent non-fluorinated or partially fluorinated organic compounds using hydrogen fluoride having an arsenic content of less than about 10 ppm is used. These and other features, aspects, and advantages of the present invention will become better understood with reference to the following description and appended claims.

DESCRIPTION

The present invention provides an improved process for the continuous preparation of perfluorinated organic compounds by electrochemical fluorination of the parent non-fluorinated or partially fluorinated organic compounds, hereinafter referred to as starting materials, using hydrogen fluoride having an arsenic content of less than about 10 ppm.

According to the invention, hydrogen fluoride having an arsenic content of preferably at most about 1 ppm of arsenic, particularly preferably at most about 0.3 ppm of arsenic, is used. This can be prepared by using particularly low-arsenic fluorspar in the preparation of hydrogen fluoride or by fractional distillation of commercial hydrogen fluoride to give a fraction rich in arsenic and a fraction low in arsenic. This hydrogen fluoride is preferably prepared by oxidizing the arsenic compounds present in commercial hydrogen fluoride and isolating a particularly low-arsenic hydrogen fluoride at the top in a distillation. As oxidizing agents, it is possible to use fluorine or hydrogen peroxide as described in U.S. Pat. No. 4,668,497 (cf. WO 88/06139).

For the purposes of the present invention, perfluorinated organic compounds are preferably perfluoroalkylsulfonyl fluorides of the general formula $C_nF_{2n+1}SO_2F$ ($n \geq 1$), e.g., perfluorobutylsulfonyl fluoride, perfluoroalkanes of the general formula ($C_nF_{2n+2}$ (where n is 1 to 10) or perfluoroalkylamines of the general formula ($C_nF_{2n+1})_3N$ (where n is 1 to 10).

The process of the invention is preferably employed for preparing perfluorobutylsulfonyl fluoride using sulfolane, sulfolene, butylsulfonyl fluoride, butylsulfonyl chloride or mixtures thereof as starting material.

The electrolysis is carried out in hydrogen fluoride, to which electrolyte salts such as sodium fluoride or sodium tetrafluoroborate (cf. U.S. Pat. No. 5,326,437) can be added. The electrode material used for the anodes is usually nickel, for the cathodes nickel or iron.

The process of the invention can be carried out in cells having a capacity of up to 4 m$^3$. The electrolyte can be circulated by pumping and cooled in order to minimize the hydrogen fluoride loss caused by evaporation. When the process of the invention is carried out industrially, the material to be fluorinated (starting material) is added continuously to the cell. The hydrogen fluoride that has been consumed can be added continuously or discontinuously during the course of the fluorination. The perfluorinated product can, if it has a boiling point of greater than about 20° C. and is insoluble in the electrolyte, be removed discontinuously or continuously from the cell. Extraction of the perfluorinated product from the electrolyte is appropriate when the perfluorinated product has a boiling point lower than about 20° C. or is readily soluble in the electrolyte. The amount of starting material added is calculated according to the equivalent of charge according to the stoichiometry of the reaction.

The starting material can be added either steadily or for periods at a time. During these periods of addition, the starting material can be metered in continuously or in portions and stoichiometrically according to the reaction equation. The lengths of the periods of addition can be varied by altering the amount added during the period.

The electrolysis is generally carried out at current densities of from about 5 to about 40 mA/cm$^2$, preferably from about 8 to about 20 mA/cm$^2$. The voltage is generally from about 5 to about 10 volts, preferably from 5 to 7 volts. The temperature should be from 0 to 20° C., preferably from about 10 to about 15° C.

The pressure under which the reaction is carried out is usually at ambient pressure of about 1 bar.

In principle, any electrochemical fluorination cell known from the prior art is suitable for the process of the invention. Examples of suitable electrochemical fluorination cells may be found, for example, in U.S. Pat. No. 2,519,983. An industrial electrolysis cell suitable for the process of the invention preferably has a volume of from about 2 to about 4 m$^3$.

As a result of the use of the low-arsenic hydrogen fluoride, the product yield and the electrode area-time yield of the electrolysis cells can be kept at a high level for long periods of time and electrode corrosion can be kept low. This considerably reduces, in particular, costly cleaning and repair measures in comparison with the processes known from the prior art.

The invention is further described in the following illustrative examples in which all parts and percentages are by weight unless otherwise indicated.

EXAMPLES

Comparative Example

For the electrochemical preparation of perfluorobutylsulfonyl fluoride, a mixture of 95% by weight of sulfolane and 5% by weight of sulfolene together with commercial hydrogen fluoride having an arsenic content of 37 ppm was fed into the electrolyte. The electrolysis voltage was 7 V, and the temperature of the electrolyte was 10° C. The perfluorinated compounds were separated from the electrolyte as a second phase. After a charge of 29.2 Ah per cm$^2$ of anode surface area, a weight loss of the nickel anode of 7.9% by weight was found. The electrode area-time yield dropped from 1.7 mg of perfluorobutylsulfonyl fluoride per cm$^2$ of anode surface area and per hour at the commencement of the electrolysis to 0.86 mg of perfluorobutylsulfonyl fluoride per cm$^2$ of anode surface area and per hour after about 5,000 hours of operation.

Example 1

The electrolysis cell used in the comparative example was provided with new nickel electrodes and operated as in the comparative example. In place of the commercial hydrogen fluoride, use was made of a hydrogen fluoride whose arsenic content over the time of the experiment was in the range from 4 to 8 ppm. After a charge of 27.2 Ah per cm$^2$ of anode surface area, the cell was switched off and the electrodes were assessed. A weight loss of the nickel anode of 1.3% by weight was found. The electrode area-time yield dropped from 1.7 mg of perfluorobutylsulfonyl fluoride per cm$^2$ of anode surface area and per hour at the beginning to 1.05 mg of perfluorobutylsulfonyl fluoride per cm$^2$ of anode surface area and per hour after 4,100 hours of operation.

Example 2

The electrolysis cell used in the comparative example was provided with new nickel electrodes and operated as in the comparative example. In place of the commercial hydrogen fluoride containing 37 ppm of arsenic, use was made of low-arsenic hydrogen fluoride whose arsenic content was less than 0.2 ppm. After a charge of 24.3 Ah per cm$^2$ of anode surface area, the cell was switched off and the electrodes were assessed. No weight loss of the nickel anode was found. The yield of perfluorobutylsulfonyl fluoride based on feed mixture used was 34%, and the electrode area-time yield remained at 1.7 mg of perfluorobutylsulfonyl fluoride per cm$^2$ of anode surface area and per hour to the end of the experiment after 4,300 hours of operation.

Although the present invention has been described in detail with reference to certain preferred versions thereof, other variations are possible. Therefore, the spirit and scope of the appended claims should not be limited to the description of the versions contained therein.

What is claimed is:

1. A process for continuously preparing perfluorinated organic compounds comprising electrochemical fluorinating of a non-fluorinated or partially fluorinated organic compound using hydrogen fluoride having an arsenic content of less than 10 ppm.

2. The process according to claim 1, wherein the hydrogen fluoride having an arsenic content of less than 1 ppm is used.

3. The process according to claim 1, wherein the perfluorinated organic compounds prepared are perfluoroalkylsulfonyl fluorides of the general formula $C_nF_{2n+1}SO_2F$, in which $n \geq 1$, perfluoroalkanes of the general formula $C_nF_{2n+2}$, in which n is 1 to 10, or perfluoroalkylamines of the general formula $(C_nF_{2n+1})_3N$, in which n is 1 to 10.

4. The process according to claim 1, wherein the non-fluorinated or partially fluorinated organic compounds are sulfolane, sulfolene, butylsulfonyl fluoride, butylsulfonyl chloride or mixtures thereof.

5. The process according to claim 1, wherein electrolyte salts are added to the hydrogen fluoride.

6. The process according to claim 1, wherein the electrolysis is carried out at current densities of from about 5 to about 40 mA/cm$^2$ and a voltage of from about 5 to about 10 volt.

7. The process according to claim 1, wherein the electrochemical fluorination is carried out at a temperature of from about 0 to about 20° C.

8. The process according to claim 1, wherein the electrochemical fluorination is carried out at a pressure of from about 0.8 to about 1.2 bar.

* * * * *